(12) United States Patent
Margalit et al.

(10) Patent No.: US 8,808,664 B2
(45) Date of Patent: Aug. 19, 2014

(54) LIPIDATED GLYCOPROTEIN PARTICLES AND METHODS OF USE

(75) Inventors: Rimona Margalit, Givatayim (IL); Dan Peer, Qiryat Ono (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 2189 days.

(21) Appl. No.: 11/632,647

(22) PCT Filed: Jul. 8, 2005

(86) PCT No.: PCT/US2005/024353
§ 371 (c)(1),
(2), (4) Date: Feb. 13, 2008

(87) PCT Pub. No.: WO2006/017195
PCT Pub. Date: Feb. 16, 2006

(65) Prior Publication Data
US 2009/0022656 A1    Jan. 22, 2009

Related U.S. Application Data

(60) Provisional application No. 60/587,028, filed on Jul. 13, 2004.

(51) Int. Cl.
| | |
|---|---|
| *A61K 51/00* | (2006.01) |
| *A61K 9/16* | (2006.01) |
| *A61K 31/7088* | (2006.01) |
| *A61K 38/00* | (2006.01) |
| *A61K 35/00* | (2006.01) |
| *A61K 31/00* | (2006.01) |
| *A61K 39/00* | (2006.01) |
| *A61K 38/43* | (2006.01) |
| *A61K 49/00* | (2006.01) |

(52) U.S. Cl.
USPC ...... 424/1.37; 424/491; 424/93.1; 424/184.1; 424/94.1; 424/9.1; 424/9.6; 514/44; 514/2

(58) Field of Classification Search
USPC .............. 424/1.37, 491, 93.1, 84.1, 94.1, 9.1, 424/9.6; 514/44, 2
See application file for complete search history.

(56) References Cited

U.S. PATENT DOCUMENTS 5,366,958 A * 11/1994 Weiner et al. ................... 514/9.3
5,401,511 A * 3/1995 Margalit ........................ 424/450
5,733,892 A * 3/1998 Sakurai et al. .................. 514/54

FOREIGN PATENT DOCUMENTS

WO    WO 03/015755 A1    2/2003

OTHER PUBLICATIONS

Gehlsen et al (Ingibition of In Vitro Tumor Cell Invasion by Arg-Gly-Asp-Containing Synthetic Peptides, 1988, Cancer Research Center, pp. 925-930).*
E.I. Chazov et al., "Endothelial cell culture on fibrillar collagen: Model to study platetlet adhesion and liposome targeting to intercellular collagen matrix", vol. 78, No. 9, Sep. 1981, pp. 5603-5607.
M. J. Fonseca et al. "Coating liposomes with collagen (M 50 000) increases uptake into liver" Biochimica et Biophysica, vol. 1279, No. 2, 1996, pp. 259-265.
C. H. Lee et al. "Biomedical applications of collagen" International Journal of Pharmaceutics, vol. 221, No. 1-2, Jun. 19, 2001, pp. 1-22.
M. Pajean et al. "Stabilization of liposome with collagen" 1992, Caplus.
K. Panduranga et al., "Recent development of collagen-based materials for medical applications and drug delivery systems" vol. 7, No. 7, 1995, pp. 623-645.
D. G. Wallace et al., "Collagen gel systems for sustained delivery and tissue engineering", Advanced Drug Delivery Reviews, vol. 55, vol. 12, Nov. 28, 2003, pp. 1631-1649.
A. L. Weiner et al., "Liposome-Collagen Gel Matrix: A Novel Sustained Drug Delivery System", Journal of Pharmaceutical Science American Pharmaceutical Association, vol. 74, No. 9, Sep. 9, 1985, p. 922-925.
Albelda et al., Integrins and other cell adhesion molecules, The FASEB Journal, 4:2868-2880 (1990).
Benita et al., Submicron emulsions as colloidal drug carriers for intravenous administration: Comprehensive physicochemical characterization, Journal of Pharmaceutical Sciences, 82(11):1069-1079 (1993).
Gottesman et al., Genetic analysis of the multidrug transporter, Annu. Rev. Genet. 29:607-49 (1995).
Larsen et al., Resistance mechanisms associated with altered intracellular distribution of anticancer agents, Pharmacology & Therapeutics, 85:217-229 (2000).
Nutt et al., Differential expression of drug resistance genes and chemosensitivity in glial cell lineages correlate with differential response of oligodendrogliomas and astrocytomas to chemotherapy, Cancer Research, 60:4812-4818 (2000).
Wolff et al., Chemosensitivity of glioma cells in vitro: a meta analysis, J. Cancer Res. Clin. Oncol., 125:481-486 (1999).
Bangham, Liposomes: the Babraham connection, Chemistry and Physics of Lipids, 64:275-285 (1993).
Dedhar et al., A cell surface receptor complex for collagen type I recognizes the Arg-Gly-Asp sequence, J. Cell Biol., 104:585-593 (1987).
Gref et al., Biodegradable long-circulating polymeric nanospheres, Science, 263:1600-1603 (1994).
Margalit et al., Liposomal drug delivery: thermodynamic and chemical kinetic considerations, Journal of Controlled Release, 17:285-296 (1991).
Ruoslahti et al., Peptides in cell adhesion research, Methods in Enzymology, 245:346-369 (1994).
Wu et al., In vivo versus in vitro degradation of controlled release polymers for intracranial surgical therapy, Journal of Biomedical Materials Research, 28:387-395 (1994).

* cited by examiner

*Primary Examiner* — San-Ming Hui
*Assistant Examiner* — Kathrien Cruz
(74) *Attorney, Agent, or Firm* — Browdy and Neimark, PLLC (57) ABSTRACT

Lipidated micro- or macroparticles are prepared by covalently linking a glycoprotein, typically collagen, with at least one lipid. An amino group in the glycoprotein is joined with a primary amine in the lipid. These particles can be used to encapsulate active ingredients, such as drugs.

21 Claims, 6 Drawing Sheets

LIPIDATED GLYCOPROTEIN PARTICLES AND METHODS OF USE

FIELD OF THE INVENTION

The present invention relates to lipidated glycoprotein particles and to the preparation and uses of microscopic and macroscopic drug delivery systems such lipidated glycoprotein particles.

BACKGROUND OF THE INVENTION

Glycoproteins such as the fibrillar collagens, types I-III, are some of the main proteins in the extracellular matrix (ECM). Collagen is attached to specific cell-surface receptors that have the amino acid sequence Arg-Gly-Asp (Albelda & Buck, 1990; Dedhar, et al., 1987; and Ruoslahti & Engvall, 1994); specifically this sequence known as the "RGD motif" has been implicated as the cell attachment site of such ECM proteins as fibronectin, vitronectin, fibrinogen, and von Willebrand factor, and is also present in type I collagen.

Because collagen is a biocompatible glycoprotein, there has been interest in developing collagenous drug carriers that can be loaded with drugs and other bioactive agents.

There are two basic classes of drug carriers (Bangham, 1993; Benita & Levy, 1993; Gref et al., 1994; and Wu et al., 1994): (1) particulate systems, such as cells, microspheres, viral envelopes, and liposomes and (2) non-particulate, usually soluble, systems consisting of macromolecules such as proteins or synthetic polymers.

Microscopic and macroscopic particulate carriers have several distinct advantages over treatment with free drugs and non-particulate carriers. They can perform as sustained-release or controlled-release drug depots, thus contributing to improvement in drug efficacy and allowing reduction in the frequency of dosing. By protecting both the entrapped-drug and the biological environment, these carriers reduce the risks of drug inactivation and degradation. Since the pharmacokinetics of free drug release from the depots are different than from directly-administered free drug, these carriers have the potential to reduce toxicity and undesirable side effects.

Despite the advantages offered, the use of currently existing drug encapsulating particulate carriers has posed some challenges which have yet to be fully overcome. For example, both macroparticulate and microparticulate drug delivery systems display limited targeting abilities; limited retention and stability in circulation; potential toxicity upon chronic administration; and an inability to extravasate. Numerous attempts have been made to bind substances such as antibodies, glycoproteins and lectins to particulate systems (e.g., liposomes, microspheres and others) in order to improve targeting ability.

Although bonding of these targeting agents to the particulate systems has met with success, the resulting modified particulate systems have not performed as hoped, particularly in vivo. Other difficulties are also present. For example, for maximal effectiveness, antibodies should be patient-specific and therefore add cost to the therapeutic regimen.

Further, not all binding between the targeting substance and the carrier is covalent. This type of bond is essential, as non-covalent binding might result in dissociation of the targeting substances from the particulate system at the site of administration, due to competition between the particulate system and the targeted components at the site. Upon such dissociation, the administered modified particulate system would likely revert to a conventional particulate system, thereby defeating the purpose of administration of the modified particulate system.

Therefore, there is a need in the art for a novel adhesive biopolymer that can serve as a particulate carrier of drugs and other bioactive agents. Such a biopolymer would be fully degradable and compatible in and with biological systems, unlike existing particulate carriers that have non-biological components. Due to the use of biocompatible raw materials, this biopolymer would be nontoxic and nonimmunogenic, unlike some of the existing carriers. (Toxicity and immunogenicity varies from one carrier to another, but is on an acceptable level in those few systems approved for clinical use.).

The novel bioadhesive polymer serving as a particulate carrier should also demonstrate high-efficiency entrapment independent of drug size up to and including proteins and genetic material, due to a "wraparound" or "induced-fit" nature. Existing particulate carriers demonstrate variable entrapment efficiencies ranging from low to high, with low efficiency of high molecular weight entities. For intended use as a depot, it would be desirable if the novel biopolymer exhibited exceptionally slow drug efflux, with a half-life in the range of 2-15 days. This would-be in contrast to the high variability seen in conventional preparations, with drug efflux ranging from fast to slow.

Additionally, it would be advantageous if the bioadhesive nature of the glycoprotein component would endow the system with the ability to adhere with high affinity to in vivo recognition sites and confer a measure of active targeting, in contrast with the conventional preparations. In conventional preparations, further carrier modification is required to endow the systems with these properties, but is not always feasible and in some cases is counter-productive to production and to the intended in vivo fate. It would be further desirable if the biopolymer comprised a glycoprotein, such as collagen, to which a lipid such as phosphatidylethanolamine were covalently linked.

SUMMARY OF THE INVENTION

It is an object of the present invention to overcome the deficiencies in the prior art.

It is another object of the present invention to provide microparticulate and macroparticulate drug/bioactive agent delivery systems that utilize adhesive biopolymers with drug-entrapping capability. When formulated with drugs or other bioactive agents, such delivery systems are expected to improve clinical outcomes, compared to the same drugs administered in their free form. Composed of naturally occurring materials, which are both biocompatible and biodegradable, the biopolymers of the present invention are used to encapsulate conventional drugs as well as other bioactive agents for a variety of therapeutic and diagnostic purposes.

This novel drug delivery technology has many advantages over other current systems. These include: high-efficiency encapsulation of large macromolecules; exceptionally slow sustained-release; significant improvement in the treatment of drug-resistant tumors; and no inflammatory response to in vivo implantation.

The present invention provides a drug delivery system for administration of a bioactive agent to an animal comprising the bioadhesive polymeric macroparticles or microparticles of the present invention.

More particularly, the micro- or macroparticles comprise the reaction product of at least one amino-containing glycoprotein with at least one lipid having a primary amino group. In a preferred embodiment, the glycoprotein is collagen and the lipid is phosphatidylethanolamine. However, any glycoprotein may be used, provided it meets the following basic criteria. The glycoprotein must be sufficiently large in size (usually 100 kDa or larger), have sufficient free amino groups (at least 5% of the amino acids should be lysine) and must possess an "RGD motif"-the amino acids arginine, glycine and aspartic acid. Examples of such glycoproteins are the collagens, fibronectin, vitronectin, fibrinogen, and von Willebrand factor.

Suitable lipids other than phosphatidylethanolamine, as would be well appreciated by those of skill in the art, may be used, for example, phosphatidyl serine, phosphatidyl choline, phosphatidyl inositol, diphosphatidyl glycerol, phosphatidic acid, lysophosphatidic acid and acylphosphatidylethanolamine.

The microparticles of the present invention are vesicular-shaped, ranging in size from about 0.5-10 microns in diameter. The macroparticles of the present invention are disk-shaped, ranging in size from about 1-20 mm in diameter.

It is contemplated that an active ingredient would be encapsulated within the micro- or macroparticles. Such active ingredients are selected from the group consisting of anti-infective agents, anti-neoplastic drugs, anti-viral agents, anti-microbial drugs, chemotherapeutic agents, anti-inflammatory agents, neuroleptics, fluorescent dyes, proteins, hormones, enzymes, cells, and nucleic acids.

The invention further provides a method of making a drug delivery system in macroparticulate form, which comprises dissolving a glycoprotein; providing a reaction vessel in which a lipid is disposed in a thin layer; buffering the lipid to a basic pH; admixing the dissolved glycoprotein in the reaction vessel; adding a crosslinker; incubating a glycoprotein and lipid and cross-linker reaction mixture, with continuous shaking, for a period of time sufficient for glycoprotein disks to form; buffering a resultant lipidated glycoprotein to a neutral pH; separating unbound glycoprotein by centrifugation; and lyophilizing a resultant lipidated glycoprotein disk. For drugs and other bioactive agents that are stable at basic pH, encapsulation may occur by adding the drug when the crosslinker is added. In a preferred embodiment, the glycoprotein is collagen and the lipid is phosphatidylethanolamine. The basic pH is typically within the range from 8-10. Preferably, the cross-linker is glutaraldehyde.

The present invention further provides a method of making a drug delivery system in microparticulate form, which comprises the same steps as used for the macroparticulate drug delivery system, but with the additional step of forming microparticles by means of the application of mechanical forces to crush the glycoprotein disks into particles.

For those drugs that are not stable at a basic pH, the invention also provides a method for making lipidated collagen disks or particles having an active ingredient entrapped therein, which comprises reconstituting lyophilized collagen disks in water and adding a powdered active ingredient, whereby the active ingredient is entrapped within the lipidated collagen disks.

The invention further provides a method for treating an animal suffering from a pathological condition, which comprises administering to the animal an effective amount of a bioactive agent encapsulated in micro- or macroparticles of a drug delivery system. The pathological condition may be, but is not limited to, cancer, bacterial infections including osteomyelitis, fungal infections, viral infections, parasite infections, prion infections, or chronic conditions such as osteoarthritis, psychosis or hypertension.

In one embodiment, the pathological condition is cancer and the bioactive agent is an anticancer drug. In a preferred embodiment, the cancer is a cancer of a central nervous system of an animal, particularly a glioma. The cancer may also be colon adenocarcinoma. In another preferred embodiment, the cancer is a metastatic cancer. The anti-cancer drug may be administered locally, or, in the case of a cancer affecting the reticular endothelial system such as lymphomas or leukemias, it may be administered systemically.

Other pathological conditions are within the scope of the method of treatment provided by the present invention. For example, in one embodiment the pathological condition is a bacterial infection and the bioactive agent is an anti-bacterial drug. Treatment of such infections as (without limitation) fungal, viral, parasite and prion infections are contemplated within the scope of the invention as well.

Chronic conditions such as osteoarthritis, psychosis or hypertension, where there are significant difficulties with patient compliance with drug regimens are also contemplated as being within the scope of the present invention. In particular, the depot formulation lends itself well to such conditions where the patient must receive a constant lifelong dose of the appropriate drug.

Use in immunization programs is another application of the present invention. When vaccination programs must rely on patients returning for "booster" injections, they are often rendered ineffective due to patient noncompliance. This is of concern particularly in developing countries. Long-acting, slow efflux of vaccine formulations encapsulated in the biopolymers of the present invention would be useful in such a context.

Additionally, the present invention provides lipidated collagen particles encapsulating a marker used in medical imaging. In a preferred embodiment, the marker is a radioactive isotope selected from the group consisting of $^{99m}$Tc, $^{127}$I, and $^{67}$Gd. The lipidated collagen particles may also be formulated to encapsulate a fluorescent molecule. A method for diagnostic imaging a site in a patient using such particles is also provided by the present invention.

Finally, the present invention also provides a method of gene delivery and short term expression of an isolated nucleic acid segment in a target cell or organ, which comprises administering to an animal in need thereof an effective amount of lipidated collagen particles encapsulating nucleic acids.

DETAILED DESCRIPTION OF THE INVENTION

The present invention provides a drug delivery system for administration of a bioactive agent to an animal comprising bioadhesive polymeric micro- or macroparticles. It is preferred that these particles comprise the reaction product of at least one amino-containing glycoprotein with at least one lipid having a primary amino group. Optionally, yet preferably, the glycoprotein is collagen and the lipid is phosphatidylethanolamine. The microparticles are generally vesicular-shaped and preferably range in size from about 0.5 to 10 microns in diameter. The macroparticles are generally disk-shaped and preferably range in size from about 1-20 mm in diameter. In a preferred embodiment, the macroparticles are about 4 mm in diameter. In another preferred embodiment, the macroparticles are about 10 mm in diameter.

Optionally, yet desirably, an active ingredient is encapsulated within the particles. Non-limiting examples of such active ingredients include anti-infective agents, anti-inflammatory agents, anti-neoplastic drugs, anti-viral agents, anti-microbial drugs including anti-bacterial and anti-fungal drugs, chemotherapeutic agents, antipsychotic drugs, imaging agents/markers such as fluorescent dyes, proteins, hormones, enzymes, cells, and nucleic acids.

The invention further provides a method of making a drug delivery system in macroparticulate form. The method comprises an initial step of dissolving a glycoprotein. Such a dissolving step may be accomplished, for example, by pre-incubation in mildly acidic pH overnight at 4° C. In a preferred embodiment, the glycoprotein is collagen.

At a time which may be simultaneous with the initial glycoprotein dissolving step, a reaction vessel in which a lipid is disposed in a thin layer on the vessel bottom and walls is provided. This disposition may be accomplished by dissolving the lipid in an organic solvent and evaporating to dryness under low pressure in a rotary evaporator. In a preferred embodiment, the lipid is phosphatidylethanolamine. Once the disposition of the lipid is achieved, the reaction mixture comprising the lipid in the reaction vessel is to be buffered to a basic pH. Optionally, the basic pH is in the range of 8-10.

The dissolved glycoprotein is then admixed into the reaction vessel. A crosslinker, such as glutaraldehyde, is then added. Bioactive agents that do not lose their activity at a basic pH may be added in this step as well.

The resultant reaction mixture is then incubated, with continuous shaking, under time and temperature conditions sufficient for the glycoprotein disks to form, for example, overnight at 4° C. The resultant lipidated glycoprotein is buffered to a neutral pH. Other ions and water-soluble additives may then be added to the mix according to need in order to elevate the ionic strength to physiological levels with ions or salts present in biological fluids such as: NaCl, KCl, $Ca^{2+}$ and $Mg^{2+}$. Any unbound glycoproteins are subsequently separated out by centrifugation at progressively higher g forces. The lipidated glycoprotein is then lyophilized, resulting in stable disks.

The present invention also provides a method of making a drug delivery system in microparticulate form. The method comprises identical steps as the method for making a drug delivery system in macroparticulate form, but with an additional step of forming stable microparticles through applying mechanical forces sufficient to crush the macroparticle disks into particles.

The present invention further provides a method for making lipidated glycoprotein macro- or microparticles having an active ingredient entrapped therein, comprising reconstituting lyophilized collagen disks in water, and adding a powdered active ingredient, whereby the active ingredient is entrapped within the lipidated collagen disks. This method is suitable for use when the active ingredient of interest would lose its biological activity at a basic pH and therefore cannot be added during the micro- or macroparticle formulation process. This method comprises reconstituting lyophilized lipidated collagen particles in water, and adding a powdered active ingredient, whereby the active ingredient is entrapped within the lipidated collagen particles.

A method for treating an animal suffering from a pathological condition is additionally furnished by the present invention, comprising administering to the animal in need thereof an effective amount of a bioactive agent encapsulated in the micro- or macroparticles of the drug delivery system of the instant invention. The pathological condition may be, but is not limited to osteoarthritis, cancer, bacterial infections including osteomyelitis, fungal infections, viral infections, parasite infections, psychoses and prion infections.

Exceptionally resistant cancers such as gliomas and colon adenocarcinomas are particularly suited for in situ therapies utilizing the treatment method of the present invention. Cancers in general are useful targets of the glycoprotein biopolymers because tumors are areas very rich in cell surface receptors, such as integrins, that bind glycoproteins such as collagen. The vicinity of a tumor is also highly enriched in extracellular matrix (ECM) proteins. Indeed, it is proposed that by blocking the receptors with the empty particles of the present invention (particles free of any therapeutic agent), inhibition of metastasis occurs because the tumor cannot use the receptors in its metastatic process.

Because the invention contemplates the use of fluorescent and radioactive markers for diagnostic and therapeutic use, the invention further provides lipidated collagen particles encapsulating a marker used in medical imaging. In a preferred embodiment, the marker may be a radioactive isotope such as $^{99m}Tc$, $^{127}I$, and $^{67}Gd$. Lipidated collagen particles encapsulating a fluorescent molecule are also contemplated to be within the scope of the invention. The present invention additionally furnishes a method for diagnostic imaging a site in a patient using the particles.

The present invention also furnishes a method of gene delivery and short term expression of an isolated nucleic acid segment to a target region comprising administering to an animal in need thereof an effective amount of lipidated collagen particles encapsulating nucleic acids. Applications of the gene therapy include, without limitation, treatment of cancer and other molecular disorders. As discussed above, cancers in general are useful targets of the glycoprotein biopolymers because these polymers home to sites rich in those cell surface receptors, such as integrins, that bind glycoproteins such as collagen. Therefore, tumors may be targeted by such polymers for therapeutic purposes.

The present invention further provides an improvement to methods for treating a given indication with a drug that is effective for treating the indication. The improvement results from the drug being administered encapsulated in lipidated glycoprotein microparticles or macroparticles, also referred to as "collagomers". For instance, in a pathological condition such as osteomyelitis (bone infection), antibiotics, e.g., antibacterials such as cephalosporins, can be locally administered. Likewise, to treat osteoarthritis, anti-inflammatory drugs, such as acetaminophen, COX-2 inhibitors (CELEBREX, ROFECOXIB, etc.), and non-steroidal anti-inflammatory drugs (NSAIDs) including aspirin, ibuprofen, naproxen, diclofenac, and ketoprofen can be administered locally by encapsulating such anti-inflammatory drugs in the collagomers of the present invention.

As used herein, the term "drug" is identical to that employed in the 26$^{th}$ Edition of Stedman's Medical Dictionary, viz., "[a] [t]herapeutic agent; any substance, other than food, used in the prevention, diagnosis, alleviation, treatment, or cure of disease."

In addition, for the purposes of the present invention, a drug may be any substance that affects the activity of a specific cell, bodily organ or function. A drug may be an organic or inorganic chemical, a biomaterial, etc. Any chemical entity of varying molecular size (both small and large) exhibiting a therapeutic effect in animals and humans and/or used in the diagnosis of any pathological condition, including substances useful for medical imaging such as fluorescent dyes and radioactive isotopes fits the above definition.

Active agents that can be delivered according to the present invention include inorganic and organic drugs without limitation and include drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immune system, reproductive system, skeletal system, autocoid systems, alimentary and excretory systems, histamine systems and the like.

An active drug that can be delivered for acting on these recipients can be water soluble or water insoluble/poorly soluble and includes, but is not limited to, anticonvulsants, analgesics, anti-Parkinson's, anti-inflammatories, calcium antagonists, anesthetics, antimicrobials, antihypertensives, antihistamines, antipyretics, alpha-adrenergic agonists, antipsychotics, alpha-blockers, biocides, bronchial dilators, beta-adrenergic-blocking drugs, contraceptives, cardiovascular drugs, calcium channel inhibitors, antidepressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, opthalmics, sedatives, steroids, sympathomimetics, tranquilizers, vaccines, vitamins, nonsteroidal anti-inflammatory drugs, angiotensin converting enzymes, polynucleotides, polypeptides, polysaccharides, and the like.

Of particular interest is the possibility of applying the drug delivery technology for use as a depot in administering drugs for chronic long-term use and for vaccination. Also, leaving a depot in place following surgery may be advantageous. In the former instance, there are significant problems with patient compliance when drugs for conditions such as hypertension or mental illnesses are prescribed. Regimes such as depot administration would be beneficial in eliminating this problem. Also, in many instances, e.g., developing nations, etc., vaccination programs are rendered ineffective as patients do not return for their "booster" immunizations. A long acting depot preparation could solve this problem.

This technology is different from that of the drug delivery technology invented by D. Peer and R. Margalit, denoted lipidated glycosaminoglycans (or gagomers)(PCT International Application No. PCT/U.S.02/25178 and U.S. Patent Application Publication U.S.2004/0241248). There are several key differences between the collagen-based particles of the present technology and the hyaluronic acid-based particles of the other technology.

The first key difference involves scale: the collagomers are on a macro-(mm) and micro-(μm) scale, whereas the gagomers are on a micro-(μm) and nano-(nm) scale. Another key difference lies in the nature of the biological recognition sites. The collagomers recognize collagen receptors and collagen-binding proteins with the RGD motif. By contrast, the gagomers recognize hyaluronic acid receptors and hyaluronic acid-binding proteins. Additionally, while the collagomers, due to their size, are most suitable for local administration and as implants, the gagomers may be used for both systemic and local administration. Finally, the collagomers display extremely slow release times, with a typical half-life from disks>15 days, while the gagomers have a slow release time, with a typical half-life 1-3 days.

The collagomers may be formulated to entrap therapeutic compositions for drug or gene therapy, or may be empty, for use as drug carriers. Results from animal studies suggest that empty collagomers may even have some therapeutic utility in treating cancer, especially metastatic cancer, by blocking the cell surface receptors to which the metastasizing tumor cells would bind.

Depending on the intended mode of administration, the compositions used may be in the form of solid, semi-solid or liquid dosage forms such pharmaceutical compositions will include the collagomer construct as described and a pharmaceutical acceptable excipient, and, optionally, may include other medicinal agents, pharmaceutical agents, carriers, adjuvants, etc. It is preferred that the pharmaceutically acceptable carrier is chemically inert to the active compounds and have no detrimental side effects or toxicity under the conditions of use.

The choice of carrier is determined partly by the particular active ingredient, as well as by the particular method used to administer the composition. Accordingly, there are a wide variety of suitable formulations of the pharmaceutical compositions of the present invention.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste using, for example, maize starch, wheat starch, rice starch, potato starch, gelatin, tragacanth, methylcellulose, hydroxypropylmethylcellulose, sodium carboxymethylcellulose, and/or polyvinyl pyrrolidine. Suitable formulations can be found in *Remington's Pharmaceutical Sciences*, 16$^{th}$ and 18$^{th}$ Eds., Mack Publishing, Easton, Pa. (1980 and 1990), and *Induction to Pharmaceutical Dosage Forms*, 4$^{th}$ Edition, Lea & Febiger, Philadelphia (1985), each of which is incorporated herein by reference.

Pharmaceutical compositions using the collagomers according to the present invention can be administered by any convenient route, including parenteral, e.g., subcutaneous, intravenous, intranasal, topical, intramuscular, intraperitoneal, etc. Alternatively or concomitantly, administration may be by the oral route.

Parenteral administration is usually characterized by injection, most typically subcutaneous, intramuscular or intravenous. Parenteral administration can be by bolus injection or by gradual perfusion over time.

Means by which the collagomers may be administered are encompassed under the rubric of drug delivery devices. The term "drug delivery device" refers to any means for containing and releasing a drug wherein the drug is released into a subject. Drug delivery devices are split into five major groups: inhaled, oral, transdermal, parenteral and suppository. Inhaled devices include gaseous, misting, emulsifying and nebulizing bronchial (including nasal) inhalers; oral includes mostly pills; whereas transdermal includes mostly patches. Parenteral includes two sub-groups: injectable and non-injectable devices. Non-injectable devices are generally referred to as "implants" or "non-injectable implants" and include, e.g., pumps and solid biodegradable polymers. Injectable devices are split into bolus injections, that are injected and dissipate, releasing a drug all at once, and depots, that remain discrete at the site of injection, releasing drug over time. Many drug delivery devices are described in Encyclopedia of Controlled Drug Delivery (1999), Edith Mathiowitz (Ed.), John Wiley & Sons, Inc.

A preferred embodiment of the drug delivery device can be a depot. As noted supra, depots are injectable drug delivery devices that may comprise polymeric and/or non-polymeric materials, and are provided in liquid, or semi-solid forms that release drug over time. "Depot" means a localized site in the body containing concentrated active agents or drugs. Examples of formulations that form depots are gels, implants, microspheres, matrices, particles, oils, liquid polymers and non-polymers, etc. A most preferred embodiment consists of the formulation in the form of a depot comprising microspheres.

EXAMPLE 1

Synthesis of Drug-Entrapping Collagomers

Two basic types of collagomers were synthesized: disk-shaped macroparticles and vesicular-shaped microparticles.
Particle Preparation Among the drugs/bioactive agents which may be entrapped in the collagomer of the present invention are: the fluorescent dye molecule fluorescein (Flu); the anti-microbial chloramphenicol (CAM), the antineoplastics doxorubicin (DOX), Mitomycin C (MMC) and vinblastine (VIN); bovine serum albumin (BSA) conjugated to the fluorescent marker fluorescein isothiocyanate (FITC) (BSA-FITC); the antiviral protein interferon 2α-(INFα) and plasmid DNA (pMC1403 from E coli).

A process for creating glycoprotein disks or particles by covalently binding a lipid having a primary amino group to an amino containing glycoprotein comprises the steps of:
(a) Dissolving a glycoprotein by pre-incubation in mildly acidic pH overnight at 4° C.;
(b) Providing a reaction vessel wherein a lipid is disposed in a thin layer on the vessel bottom and walls, e.g., by dissolving the lipid in an organic solvent and evaporating to dryness under low pressure in a rotary evaporator;
(c) Buffering the reaction mixture of the lipid to a basic pH (8-10);
(d) Admixing the dissolved glycoprotein to the reaction vessel and adding a crosslinker such as glutaraldehyde (GAD) (at this point, drugs which do not lose their biological activity at basic pH levels may be added);
(e) Incubating the buffered reaction mixture, with continuous shaking, for a period of time sufficient for the collagen disks or particles to form (such as overnight at 4° C.);
(f) Buffering the lipidated collagen to neutral pH and adding other ions and water-soluble additives (such as NaCl, KCl, $Ca^{2+}$ and $Mg^{2+}$) according to need;
(g) Separating the unbound glycoproteins by centrifugation at progressively higher g forces;
(h) Lyophilizing the lipidated glycoprotein, which results in a stable disk; and
(i) Forming, when desired, stable microparticles, through applying mechanical forces to crush disks into particles.

Entrapment of Bioactive Agents

There are two ways by which bioactive agents such as drugs can be entrapped in the collagomers:
1. (a) Dissolving the drug/bioactive agent of interest in ion-free pure water; and
(b) Reconstituting the carrier from the lyophilized dry powder obtained in step I(h) above (when no drug was added by step I (d)) by re-hydrating the powder with solution from 1(a) above; or
2. For drugs that are stable in basic pH-dissolving the drug/bioactive agent of interest in step I(d) above.

EXAMPLE 2

Structural Properties of Disks and Particles

Investigation of the structural properties of the macroparticulate disks and microparticulate vesicles were focused on the collagomer itself and on chemical bonding within it. Scanning electron microscopy (SEM) was performed.

Figure 1:
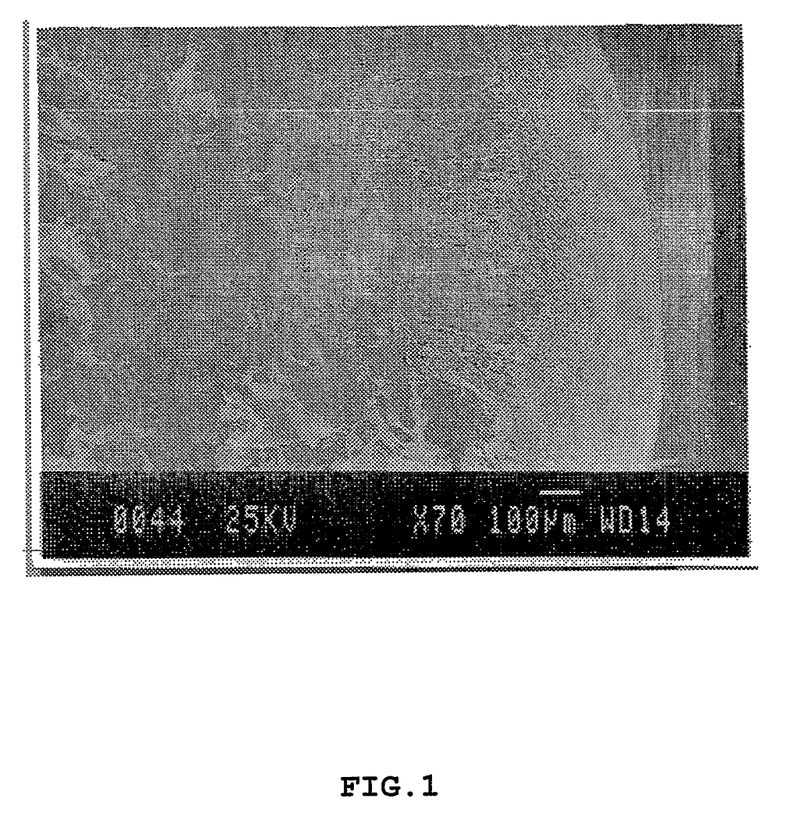
FIG. 1 is a scanning electron micrographic view into a collagen disk, showing the dense surface area and the porous nature of its interior.

FIG. 1 is an EM cross-sectional view of a disk, showing a dense surface area and the porous nature of its interior. The disk sizes were measured by electronic calipers and typical size distribution were between 1-20 mm in diameter. The disks were made by the process of Example 1 using type I collagen as the glycoprotein and phosphatidylethanolamine as the lipid and stopping the reaction after step (h).

Figure 2:
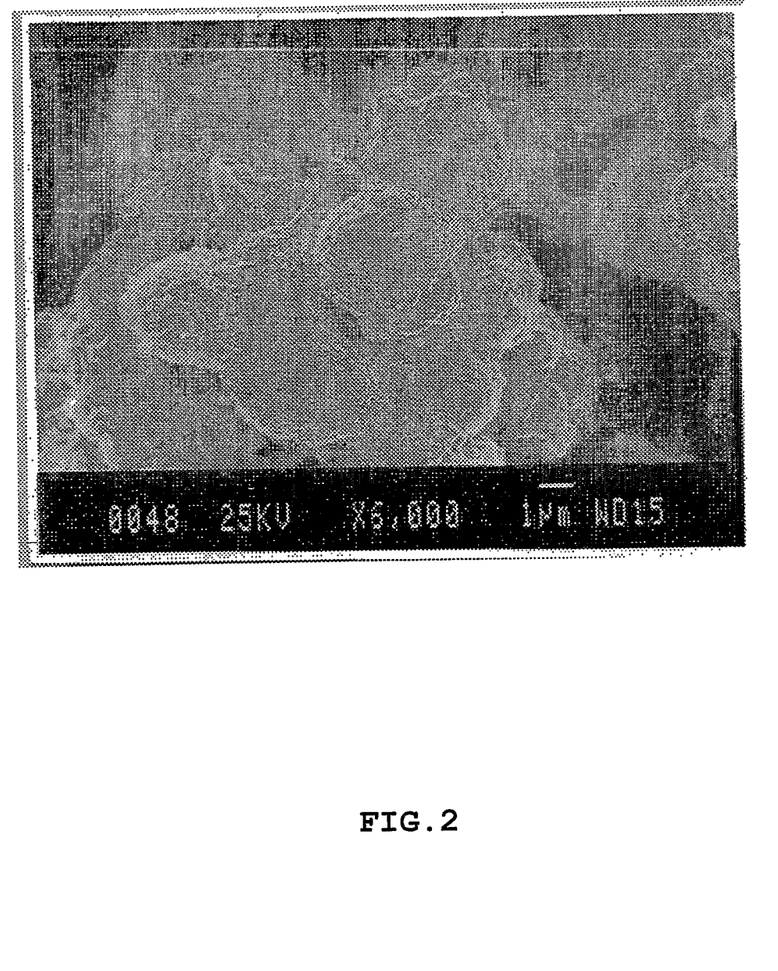
FIG. 2 shows collagen particles with an average size distribution of 0.5-10 μm, also using scanning electron microscopy.

FIG. 2 shows microparticles with an average size distribution of 0.5-10 μm in diameter. Size distribution was further confirmed by an ALV-NIBS particle size analyzer (ALV-GmbH, Langen/Germany). The microparticles were made by treating the disks of FIG. 1 according to step (i) of the particle preparation process, where disks were crushed by mechanical forces into microparticles.

EXAMPLE 3

Physicochemical Characterization

Efficiency of entrapment of drugs/bioactive agents in the collagen disks or particles, and kinetics of drug efflux for small molecular weight drugs was determined utilizing absorption spectra (mostly in an ELISA plate reader), fluorescence emission spectra (mostly in a fluorescence plate reader), and HPLC. Half-life data was processed according to a theoretical framework previously developed for liposomes (Margalit et al., 1991), incorporated herein in its entirety) which yields the rate constant for drug efflux. Typical results of the efficiency of entrapment are listed in Tables 1 and 2, for the particles and disks, respectively.

TABLE 1

Collagen particles (0.5-10 μm in diameter)

| Drug | % Entrapment | Slow release (half-life) |
|---|---|---|
| Low Molecular weight Drugs | | |
| DOX | 71.9 ± 0.4 | 13 days |
| MMC | 67.3 ± 2.1 | 6 days |
| CAM | 94.1 ± 0.8 | 15 days |
| Flu | 95.6 ± 2.8 | 9 days |
| High Molecular weight Drugs | | |
| BSA | 82.0 ± 2.3 | |
| Insulin | 91.2 ± 0.7 | |
| Interferon alpha | 88.2 ± 5.1 | |
| DNA | 80.7 ± 2.1 | |

TABLE 2

Collagen Disks (1-20 mm in a diameter)

| Drug | % Entrapment | Slow release (half-life) |
|---|---|---|
| Low Molecular weight Drugs | | |
| DOX | 78.4 ± 2.4 | 15 days |
| MMC | 80.2 ± 1.0 | 12 days |
| CAM | 89.5 ± 1.4 | 19 days |
| High molecular weight drugs | | |
| BSA | 87.5 ± 1.7 | 17 days |
| Insulin | 89.4 ± 2.3 | 21 days |
| Interferon alpha | 93.6 ± 1.3 | 24 days |
| DNA | 85.1 ± 4.3 | |

The results shown in these tables demonstrate that both small and large drugs can be entrapped in collagen disks and particles with high efficiency. Efficiency of entrapment is exceptionally high for the large molecules compared to other particulate carriers such as liposomes and microspheres. Typical examples of the kinetics of drug efflux from the disks and from the particles is shown in Tables 1 and 2 for small as well as large molecules. In all cases the systems perform as sustained-release drug depots, as desired, with most half-lives on the order of 6-24 days, depending on the drug itself and the degradation rate of the disks and particles.

EXAMPLE 4

Confocal Microscopy

Figure 3:
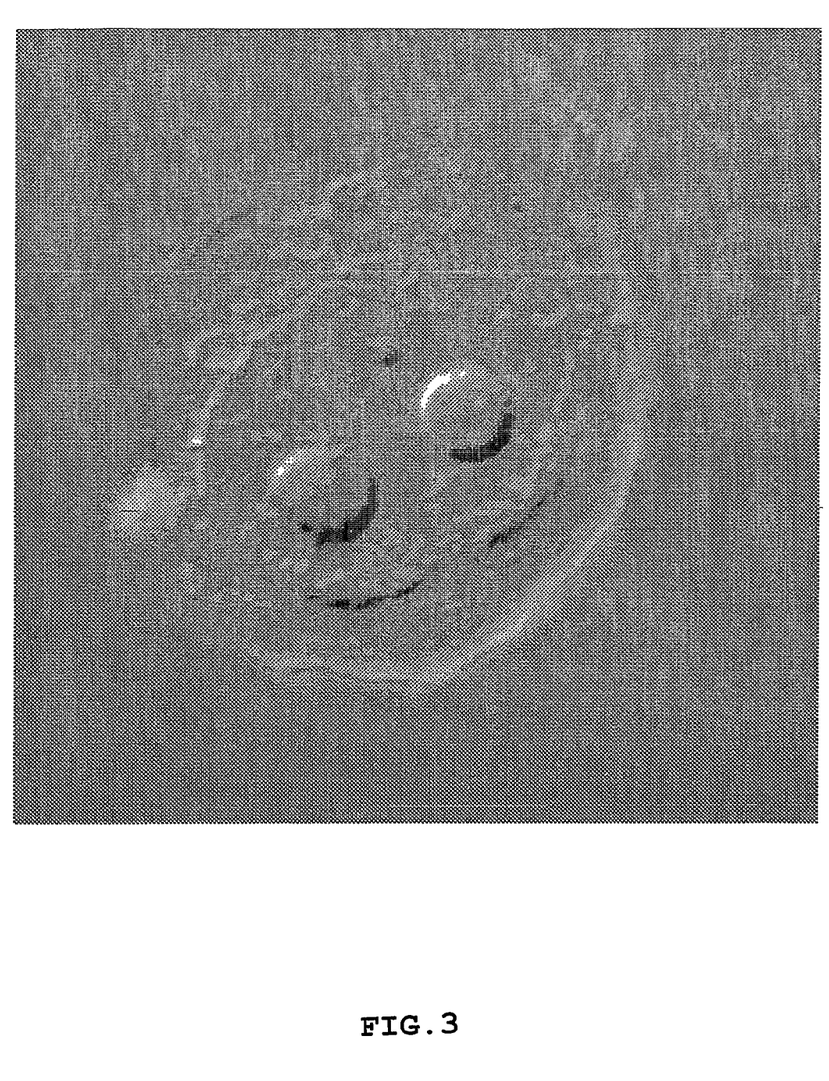
FIG. 3 is confocal microscopy of PANC-1 (human pancreatic adenocarcimona) cells showing collagen particles entrapping protein (BSA-FITC). Cells were seeded into a 6 well plate. After 24 hours the collagen-particles entrapping BSA-FITC were added to the cells and incubated for 1 hour at room temperature following three washings with PBS to separate the unbound particles from the cells. Then the cells underwent fixation for confocal microscopy and pictures were taken with a Zeiss camera.
Figure 4:
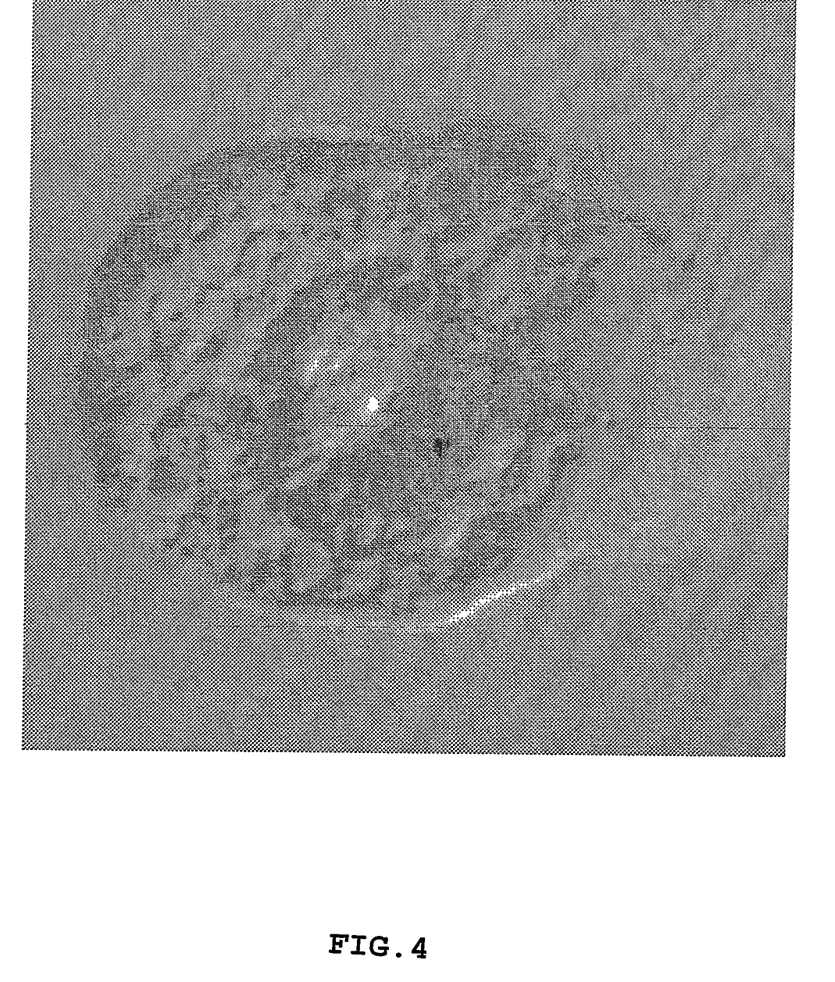
FIG. 4 is confocal microscopy of C26 cells from mouse colon adenocarcimona showing collagen particles entrapping protein (BSA-FITC). Cells were seeded into a 6 well plate. After 24 hours the collagen-particles entrapping BSA-FITC were added to the cells and incubated for 1 hour at room temperature following 3 washing with PBS to separate the unbound particles from the cells. Then the cells underwent fixation for confocal microscopy and pictures were taken with a Zeiss camera.

BSA-FITC was entrapped in the particles. Using confocal microscopy it was found, as shown in FIGS. 3 and 4, that the particles attach to the adenocarcinoma cells but do not enter. The two cell lines are PANC-1 (human pancreatic adenocarcimona) and C26 (mouse colon adenocarcimona), for FIGS. 3 and 4, respectively.

EXAMPLE 5

Biological Activity: In Vitro Toxicity Studies

Figure 5:
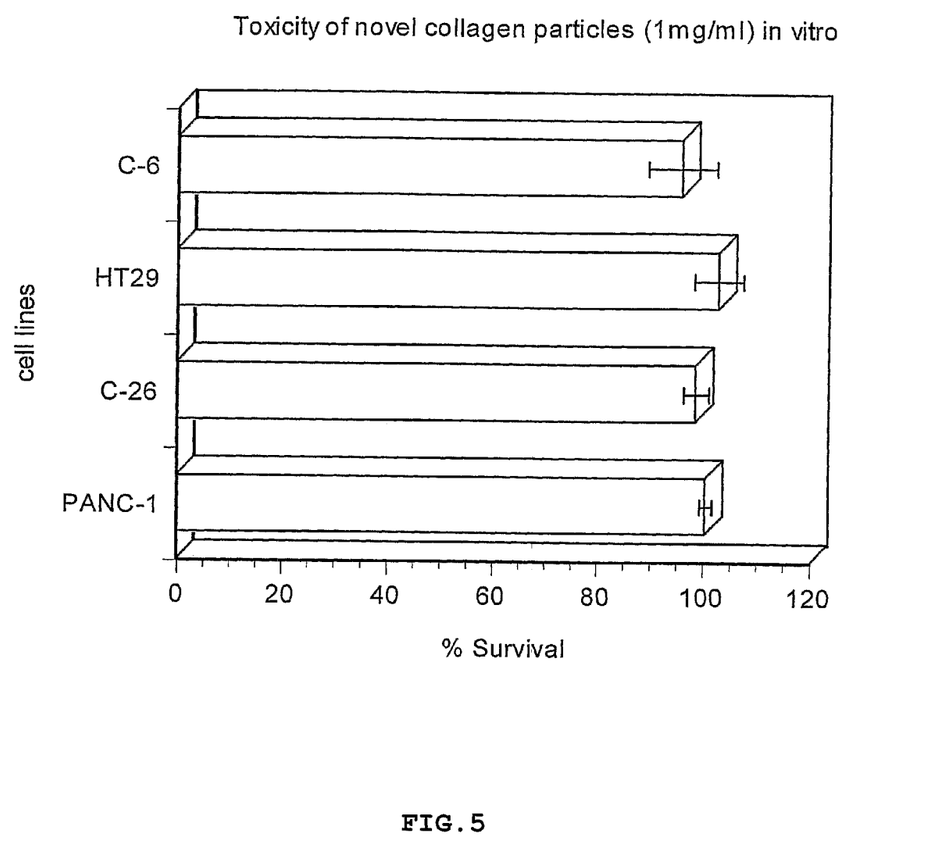
FIG. 5 shows toxicity results for one concentration of drug-free collagen particles (1 mg/ml), indicating that the particles alone display no toxicity. In vitro toxicity was assayed by the MTT method (Wolff et al., 1999; and Nutt, 2000) on four types of cell lines. The cell lines used were C6, a rat glioblastoma cell line; HT29, a human colon adenocarcimona cell line; C26, a mouse colon adenocarcimona cell line; and PANC-1m a human pancreatic adenocarcimona cell line. Each bar is an average of three independent experiments; each experiment consisted of 60-64 repeats. The error bars represent the respective standard deviations.

Drug-free collagen particles were tested for toxicity in cell cultures. Four cell lines were tested: the rat glioma line C6; the human colon adenocarcimona HT29 cell line; the human pancreatic adenocarcimona PANC-1 cell line; and the mouse colon adenocarcimona C26 line. In all cases, the collagen particles were found to have no toxicity over the 100-fold concentration range of 0.02 to 2 mg/ml polymer. FIG. 5 demonstrates those findings for one concentration of drug-free collagen particles (1 mg/ml).

Particles were also tested for their toxicity to noncancerous cell lines, the NIH 3T3 mouse fibroblast cell line (results not shown). No toxicity was observed.

EXAMPLE 6

Biological Activity: Treatment of Multi-Drug Resistant cell lines originating from tumors Poor response to chemotherapeutic drugs due to drug resistance and clinically challenging location are among the major causes for the frequent failures in treatment of brain and colon tumors, especially gliomas (Wolff et al., 1999; and Nutt, 2000), and colon adenocarcinoma. The poor drug response is due in part to lack of access, and in part to inherent multidrug resistance (MDR) (Gottesman, et al., 1995; and Larsen et al., 2000). In brain tumors, MDR is an impediment even in cases where access to the tumor has been provided, for example by local administration or by provision of a drug depot at the end of a surgical procedure. Similar difficulties are observed in the case of colon adenocarcinoma.

In this prevalent drug resistance mechanism, which appears in both an acquired and inherent mode, the drugs do not lose their intrinsic toxic activity, nor have the resistant cells found a way to metabolize the drugs into nontoxic entities. Rather, any drug that enters the cell through passive diffusion across the cell membrane is actively pumped out, reducing intracellular levels below their lethal threshold.

The glioma C6 line, which displays inherent MDR, and the two colon adenocarcimona cell lines in current use (HT29-human and C26-mouse) served as model systems for testing whether treatment with collagen particles entrapping a chemotherapeutic drug (doxorubicin, DOX) would offer any advantage over a similar treatment with the free drug.

Cells were seeded onto 96 well plates, and the experiment was initiated at semi-confluency, usually 24 hours post seeding. For the test system, cells were given a selected dose of the drug of choice, which was entrapped in a collagen particle formulation (washed of excess free drug prior to use). The controls were given the same dose of free drug, and a dose of drug-free collagen particles at a dose similar to that of the test system. Cell survival was determined 24-28 hours post-treatment, using the MTT assay (Nutt, et al. 2000; and Larsen et al., 2000).

Figure 6A:
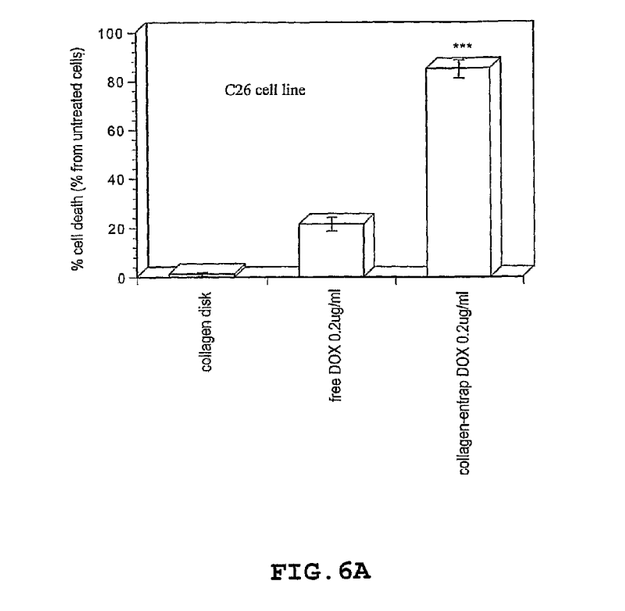
FIGS. 6A-6C show results for three cell lines, C26 (FIG. 6A), HT29 (FIG. 6B) and C26 (FIG. 6C), in terms of response to chemotherapeutic drugs encapsulated in collagen particles. The bars represent 60-64 repeats and the error bars represent the standard deviation. Three asterisks (***) indicate $p<0.001$.
Figure 6B:
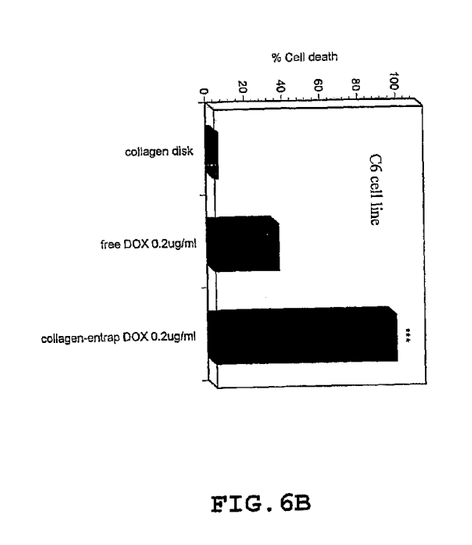
Figure 6C:
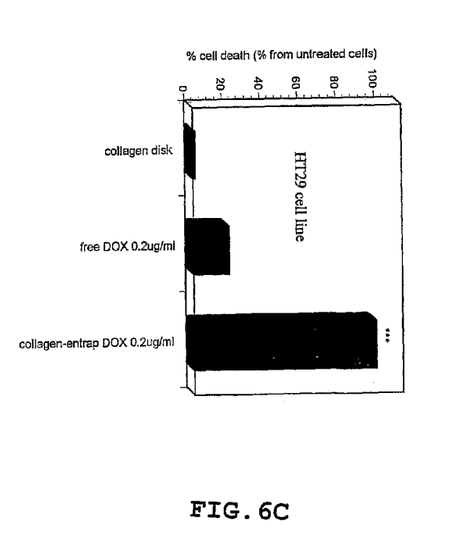

Results for three cell lines (C6, HT29 and C26) are shown in FIGS. 6A-6C in three data sets. The data for the free particles (left-most bar in each of the three data sets) is an additional confirmation that the collagen particles are non-toxic. The responses to free drug (DOX) shown in the middle bar of each data set, are typical for the inherent form of MDR.

Replacing the free drug with the same dose of collagen-particles-entrapped drug generated a dramatic difference, as seen by the right-hand bar in each data set. For each of the three cell lines, the novel formulation generates a 3-4 fold increase in cell death, compared to the corresponding free drug. Because of the non-toxic nature of the free particle, it is assumed that these results demonstrate the tumoricidal properties of the collagomers.

In theory, all that is required to overcome MDR is to find a way to elevate intracellular doses of a chemotherapeutic drug above the lethal threshold. The traditional approach has been to reduce the pumping by using reversal agents known as chemosensitizers. While several such agents have been identified—most prominent among them verapamil—they are not yet in clinical use for the treatment of cancer. This is due to the fact that these chemosensitizers cannot be used in the clinic, since dose levels that cause unacceptable adverse effects and toxicity would be required. It is important to note that such treatment would require careful orchestration as both active entities, the chemotherapeutic drug and the chemosensitizer, must reach the target together. This is not a simple matter in clinical practice.

However, another way to elevate the intracellular drug dose is to increase influx of drug, in terms of magnitude and duration thereof. It is suggested that the outstanding increase in drug response generated by the drug-entrapping particles occurs by increasing influx. The bioadhesive nature of the collagen-particles positions them as drug depots bound to the cell membrane, which should increase the magnitude of the electrochemical gradient of the drug across the cell membrane (compared to free drug), and the time span during which drug entry occurs. Efficacious cancer treatment could therefore require only one entity, the drug-collagomer formulation, which should be an advantage over the drug and chemosensitizer combination.

It is suggested that the potential of overcoming MDR that has emerged from the present studies is not restricted to the C6, HT29 and C26 cell lines, but is general to other MDR cases, both inherent and acquired. Moreover, these new formulations may also benefit non-resistant tumors, by allowing successful treatment with significantly lower drug doses.

EXAMPLE 7

In vivo Toxicity

The question of whether these novel carriers are toxic in vivo was investigated in two strains of mice and in one strain of rats. Studies were performed separately for the collagen disks and for the particles.

Experiment 1. Collagen disks were implanted in the right flanks of four C57BL/6 mice. The size of each collagen disk was 4 mm in diameter. The mice were observed for 2 months and assessed for clinical indication of inflammatory reactions at the implanted site. No inflammatory reaction was observed in those mice.

Experiment 2. Larger collagen disks (an average of 10 mm in diameter) were implanted in the right flanks of two pigmented rats. As in the case of the mice above, there were no clinical indications of any inflammatory reaction at the site of the operation, as observed over a period of two months. At the end of two months, one rat was sacrificed, and an incision was made at the implant location, in order to view the internal placement of the disk. The disk was found adhered to muscle tissue and was almost at its original size. The internal tissues were clear of inflammation, and there was no capsule build-up around the implanted disk.

Experiment 3. Collagen particles were administrated intravenously into the tail vein of four BALB/c mice. No toxicity was observed over 30 days.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Albelda, S M, and Buck, C A., *FASEB J.* 4:2868-2880 (1990)
Bangham, A. D., *Chem. Phys. Lipids,* 64:275-285 (1993)
Benita S. and Levy M Y, *J. Pharmaceutical, Sciences* 82:1069-1079 (1993)
Dedhar, S., Ruoslahti, E., and Pierschbacher, M D., *J Cell Biol,* 104:585-593 (1987)
Gottesman, M M, Hrycyna, C A, Schoenlein, P V, Germann, U A and Pastan, I., *Annu. Rev. Genet.* 29:607-649 (1995)
Gref, R., Minamitake, Y., Peracchia, M T,. Trubetskov, V,. Torchilin, V and Langer R., *Science* 263:1600-1603 (1994)
Larsen, A K, Escargueil, A E and Skladanowski, A., *Pharmacol. Ther.* 85:217-229 (2000)
Margalit R, Alon R, Lindenberg M, Rubin I, Roseman T J, and Wood, RW, *J. Controlled Release,* 17:285-296 (1991)
Nutt C L, *Cancer research,* 65:4812-4818 (2000)
Ruoslahti, E., and Engvall E., editors. Methods in Enzymology vol. 245, Extracellular matrix components. Academic press, San Diego, (1994)

Wolff J E, Trilling T, Molenkamp G, Egeler R M, Jurgens H, *J. Cancer Res. Clin. Oncol.*125, 481-486 (1999)

Wu et al., *J. Biomed. Mater. Res.* 28: 387-395 (1994)

What is claimed is:

1. A lipidated glycoprotein microparticle or macroparticle having a solid porous interior, comprising the reaction product of at least one amino-containing glycoprotein covalently bound with at least one lipid having a primary amino group.

2. The lipidated glycoprotein microparticle or macroparticle of claim 1, wherein the lipid is phosphatidylethanolamine.

3. The lipidated glycoprotein microparticle or macroparticle of claim 1, wherein the glycoprotein is collagen.

4. The lipidated glycoprotein microparticle or macroparticle of claim 1, consisting of microparticles ranging in size from about 0.5 to about 10 microns in diameter.

5. The lipidated glycoprotein microparticle or macroparticle of claim 1, wherein a drug or other biologically active ingredient is encapsulated within the microparticles or macroparticles.

6. The lipidated glycoprotein microparticle or macroparticle of claim 5, wherein the drug or other biologically active ingredient is selected from the group consisting of anti-infective agents, anti-cancer drugs, anti-neoplastic drugs, anti-fungal agents, anti-viral agents, anti-microbial drugs, anti-parasite drugs, chemotherapeutic agents, anti-inflammatory agents, agents suitable for treating prion infections; anti-psychotics, vaccines, fluorescent dyes, proteins, hormones, enzymes, cells, and nucleic acids.

7. The lipidated glycoprotein microparticle or macroparticle of claim 1, consisting of a macroparticle ranging in size from about 1 mm to about 20 mm in diameter.

8. The lipidated glycoprotein macroparticle of claim 7, wherein the macroparticle is about 4 mm in diameter.

9. The lipidated glycoprotein macroparticle of claim 7, wherein the macroparticle is about 10 mm in diameter.

10. A method of preparing the lipidated glycoprotein macroparticle of claim 1, comprising the steps of:
    (a) dissolving a glycoprotein;
    (b) providing a reaction vessel in which a lipid is disposed in a thin layer;
    (c) buffering the lipid to a basic pH;
    (d) admixing the dissolved glycoprotein in the reaction vessel;
    (e) adding a crosslinker, and optionally adding a bioactive agent stable at a basic pH;
    (f) incubating the glycoprotein and lipid and cross-linker reaction mixture, with continuous shaking, for an amount of time and under temperature conditions sufficient for lipidated glycoprotein disks to form;
    (g) buffering a resultant lipidated glycoprotein disk to a neutral pH;
    (h) separating unbound glycoprotein by centrifugation; and
    (i) lyophilizing the resultant lipidated glycoprotein disk to produce the lipidated glycoprotein macroparticles.

11. The method of claim 10, wherein the lipid is phosphatidylethanolamine.

12. The method of claim 10, wherein the glycoprotein is collagen.

13. The method of claim 10, wherein the basic pH is in a pH range of 8-10.

14. The method of claim 10, wherein the cross-linker is glutaraldehyde.

15. The method of claim 10, wherein the amount of time and temperature conditions sufficient for disks to form is overnight at 4° C.

16. The method of claim 10, further comprising the step of forming microparticles by means of the application of mechanical forces to crush the lipidated glycoprotein disks into microparticles.

17. The method of claim 10, wherein the lipidated glycoprotein disks have a biologically active ingredient entrapped therein, and wherein the lyophilized glycoprotein disks are reconstituted in water, and a powdered biologically active ingredient is added, whereby the active ingredient is entrapped within the lipidated glycoprotein disks.

18. The method of claim 17, comprising the steps of reconstituting lyophilized microparticles in water, and adding a powdered active ingredient, whereby the active ingredient is entrapped within the microparticles.

19. The lipidated glycoprotein microparticle or macroparticle of claim 1, wherein said at least one amino-containing glycoprotein comprises an RGD motif of amino acid sequence Arg-Gly-Asp.

20. The lipidated glycoprotein microparticle or macroparticle of claim 1, wherein said at least one amino-containing glycoprotein is 100 kDa or larger and has at least 5% of its amino acids as lysine.

21. The lipidated glycoprotein macroparticle of claim 1, wherein the macroparticle has a dense surface area.

* * * * *